United States Patent [19]

Sakata et al.

[11] Patent Number: 5,545,400

[45] Date of Patent: Aug. 13, 1996

[54] DEODORANT METHOD

[75] Inventors: Masakazu Sakata, Hirakata; Hiroyuki Fujii, Katano; Yuji Hamada, Kadoma; Kenichi Shibata, Hashimoto; Yoshitaka Nishio, Neyagawa, all of Japan

[73] Assignee: Sanyo Electric Co., Ltd., Osaka, Japan

[21] Appl. No.: 458,031

[22] Filed: Jun. 1, 1995

Related U.S. Application Data

[63] Continuation of Ser. No. 188,700, Jan. 31, 1994, abandoned.

[30] Foreign Application Priority Data

Feb. 2, 1993 [JP] Japan .................................. 5-015486
Dec. 14, 1993 [JP] Japan .................................. 5-313514
Dec. 17, 1993 [JP] Japan .................................. 5-318070

[51] Int. Cl.[6] ........................................................ B61L 9/01
[52] U.S. Cl. ................. 424/76.21; 534/684; 534/686; 534/698; 534/707; 534/710; 534/770
[58] Field of Search .................................. 534/684, 686, 534/698, 707, 710, 770; 424/76.1, 76.21

[56] References Cited

FOREIGN PATENT DOCUMENTS 64-20852A    1/1989   Japan .
1-33139A     2/1989   Japan .
1-110365A    4/1989   Japan .
2-88068A     3/1990   Japan .
3-111054A    5/1991   Japan .

OTHER PUBLICATIONS

Anderson et al, *Anal. Chim. Acta*, 39 (1967) 469–477.
Cheng et al, *Analytical Chemistry*, 27 (5), 1955, 782–785.
Geary et al, *Anal. Chim. Acta*, 27 (1962) 71–79.

*Primary Examiner*—Fiona T. Powers
*Attorney, Agent, or Firm*—Armstrong, Westerman, Hattori, McLeland & Naughton

[57] ABSTRACT

A deodorant containing an azo metal complex expressed by the following structural formula 1, which is produced by mixing a solution in which azo compounds to be ligands are dissolved with a solution in which a metal salt is dissolved:

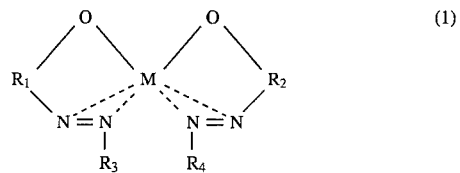

In the structural formula 1, M represents a metal element, $R_1$ and $R_2$ represent aromatic compounds, which may be the same or different from each other, and $R_3$ and $R_4$ represent aromatic compounds or heterocyclic compounds, which may be the same or different from each other. In addition, either one or both of nitrogen atoms in an azo base in each of the legends may be coordinated to the metal M.

11 Claims, 1 Drawing Sheet

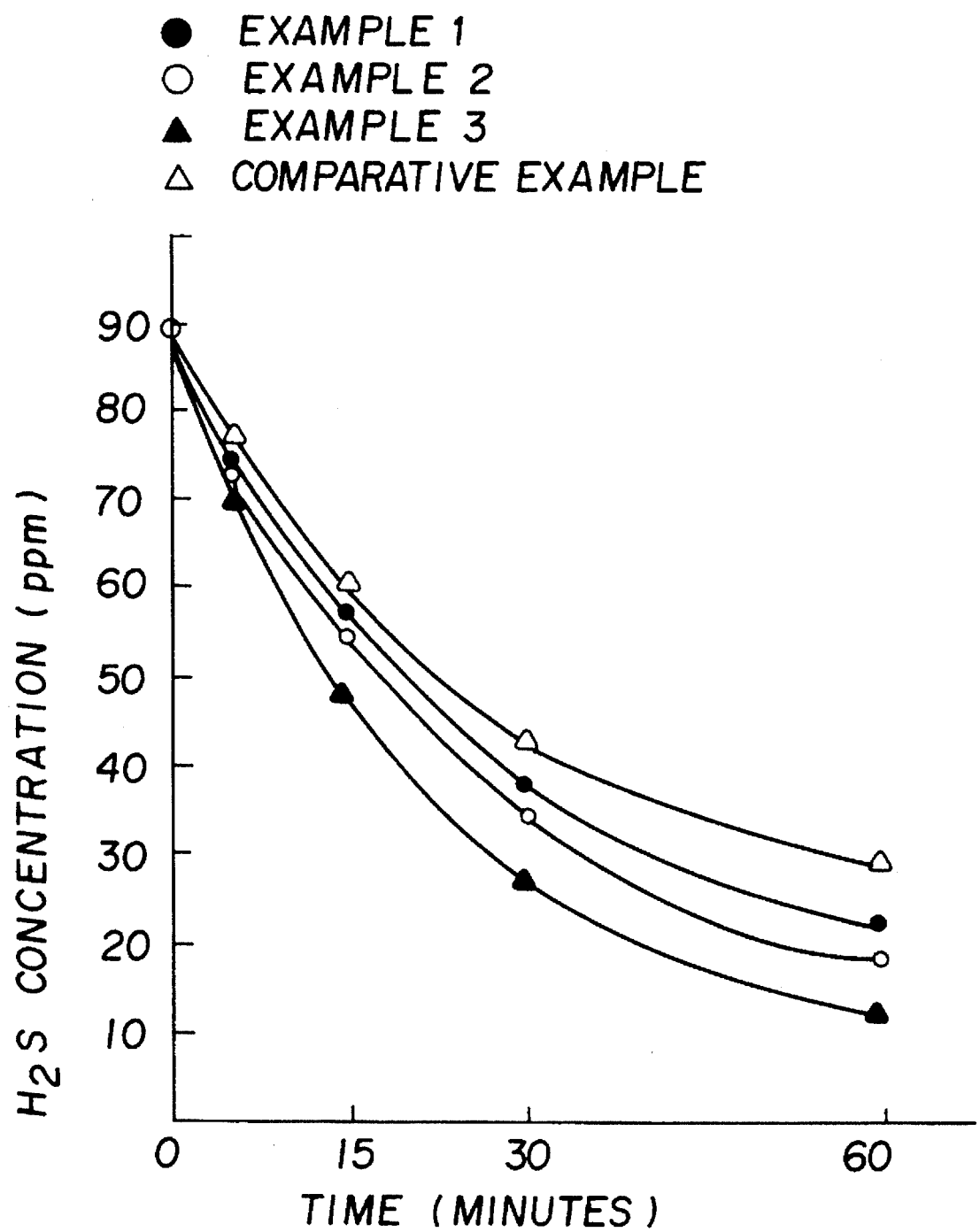

DEODORANT METHOD

This application is a continuation of application Ser. No. 08/188,700 filed Jan. 31, 1994, now abandoned.

BACKGROUND OF THE INVENTION

1. Field of the Invention

The present invention relates generally to a deodorant used for removing an odorous material which causes a malodor or the like, and particularly, to a deodorant having an azo metal complex as an active principle and capable of oxidizing the above described odorous material in air to remove the same simply and efficiently and a method of producing such a deodorant.

2. Description of the Prior Art

An odorous material which causes a malodor or the like is generally harmful in environmental sanitation, and is liable to injure human health. Accordingly, attempts to remove such an odorous material have been conventionally made. Particularly in recent years improvement of the comfortable environment has been desired, so that it has been strongly desired to fully remove the above described odorous material.

In removing the odorous material which causes a malodor or the like, various methods have been conventionally used. Examples of the methods generally used include a method of masking the odor of the odorous material using a perfume or the like by the odor of the perfume or the like and canceling the odors to destroy the odor of the odorous material, a method of diffusing the odorous material outward by ventilation to remove the same, a method of adsorbing the odorous material on a porous material such as activated carbon or zeolite to remove the same, a method of neutralizing the odorous material by acids or alkalies, a method of oxidizing or reducing the odorous material by an oxidizing agent or a reducing agent, and a method of biochemically treating the odorous material by microbes or the like.

In the method of destroying the odor of the odorous material using a perfume or the like, however, the odorous material itself still exists. Accordingly, a problem in environmental sanitation caused by the odorous material remains. In addition, other problems are encountered. For example, another malodor is emitted when the odorous material and the perfume are mixed with each other.

In the method of removing the odorous material by ventilation, the odorous material is diffused outward. Accordingly, such a method cannot be used in a closed space. In addition, the odorous material is discharged outward. Consequently, some problems are encountered. For example, the external environment is harmed, to cause secondary contamination.

In the method of adsorbing the odorous material on a porous material such as activated carbon to remove the same, the amount of the odorous material which can be adsorbed on the porous material is limited, thereby to make it impossible to stably remove the odorous material for a long time and makes it difficult to reproduce and use the porous material on which the odorous material is adsorbed, resulting in high cost.

In the method of neutralizing the odorous material using acids or alkalies, suitable acids or alkalies corresponding to the odorous material must be selected and used, so that the operation is laborious, and problems exist in safety and cost.

In the method of biochemically treating the odorous material using microbes, the speed at which the odorous material is treated is generally very high, so that it takes long and it cost much for deodorizing.

Therefore, in recent years a deodorant using metal phthalocyanine or a metal complex obtained by coordinating a Schiff base to a metal has been developed, as disclosed in, for example, Japanese Patent Laid-Open Gazette Nos. 111054/1991 and 20852/1989.

In the above described deodorant, the oxidation-reduction reaction in the above described metal complex is utilized, and the metal complex is used as a catalyst to oxidize the odorous material to change the same into an odorless material as the oxidized state of a central metal in the metal complex is changed.

In the case of the deodorant using metal phthalocyanine, however, if metal phthalocyanine is used without any change as disclosed in Japanese Patent Laid-Open Gazette No. 111054/1991, the reaction speed at which the odorous material is oxidized to be changed into an odorless material is low, thereby to make it impossible to obtain a sufficient deodorizing effect.

In Japanese Patent Laid-Open Gazette No. 111054/1991, therefore, metal phthalocyanine is used in the state of an aqueous solution together with silicon or the like in order to obtain a sufficient deodorizing effect using metal phthalocyanine. If metal phthalocyanine is used in the state of an aqueous solution, however, the place where it is used, the way it is used, and the like are limited.

Furthermore, in the case of the deodorant utilizing a metal complex obtained by coordinating a Schiff base to a metal disclosed in Japanese Patent Laid-Open Gazette No. 20852/1989, a certain degree of deodorizing effect is obtained even if the metal complex is not used in the state of an aqueous solution, unlike the above described case of metal phthalocyanine. However, the effect is not still sufficient.

SUMMARY OF THE INVENTION

An object of the present invention is to allow, in a deodorant and particularly, a deodorant for oxidizing an odorous material which causes a malodor or the like using a metal complex to change the same into an odorless material, the odorous material which causes a malodor or the like to be efficiently removed even if the metal complex is not used in the state of an aqueous solution.

Another object of the present invention is to allow the above described deodorant to be produced simply and efficiently.

In the deodorant according to the present invention, an azo metal complex expressed by the following structural formula 1 is contained.

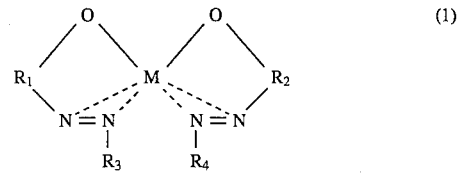

In the above described azo metal complex expressed by the foregoing structural formula 1, M may be a metal element, for example, a transition metal element such as Mn, Fe, Co, Ni or Cu. In addition, $R_1$ and $R_2$ may be aromatic compounds, which may be the same or different from each other. Further, $R_3$ and $R_4$ may be aromatic compounds or heterocyclic compounds, which may be the same or different from each other.

Furthermore, in the azo metal complex expressed by the foregoing structural formula 1, either one or both of nitrogen atoms in an azo group in each of ligands may be coordinated to the metal M.

In such a deodorant, the azo metal complex expressed by the foregoing structural formula 1 is exerted as a catalyst on the odorous material which causes a malodor or the like, and the odorous material is simply oxidized to be efficiently changed into an odorless material as the oxidized state of the above described metal M in the azo metal complex is changed, thereby to obtain a sufficient deodorizing effect even if the azo metal complex is not used in the state of an aqueous solution, unlike metal phthalocyanine.

According to the present invention, in producing the azo metal complex expressed by the structural formula 1 in the above described deodorant, azo compounds to be ligands are dissolves in alcohol, and a metal salt with the above described metal M is dissolved in alcohol or water. A solution in which the azo compounds are dissolved and a solution in which the metal salt with the metal M is dissolved are mixed with each other, and are agitated while being heated under the reflux conditions, to deposit the azo metal complex expressed by the foregoing structural formula 1.

In the above described manner, the azo metal complex expressed by the structural formula 1 in the above described deodorant is produced simply and efficiently.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a diagram showing the concentration changes of hydrogen sulfide in a case where hydrogen sulfide is deodorized using deodorants in examples 1 to 3 and a comparative example in the present invention.

DESCRIPTION OF THE PREFERRED EMBODIMENT

Preferred examples of a deodorant and a producing method therefor according to the present invention will be described in detail.

In the deodorant according to the present invention, it is preferable that an azo metal complex expressed by the foregoing structural formula 1 is exerted on an odorous material to allow the odorous material to be efficiently oxidized, and the azo metal complex is stable.

Therefore, it is preferable that a metal M in the foregoing structural formula 1 is a transition metal element such as Mn, Fe, Co, Ni or Cu.

Furthermore, $R_1$ and $R_2$ in the foregoing structural formula 1 may be aromatic compounds as described above. However, it is preferable that the aromatic compound has electron donative properties. Examples are compounds as expressed by the following structural formulas 2 to 7.

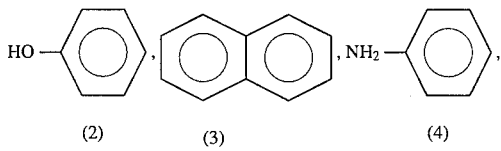

(2) (3) (4)

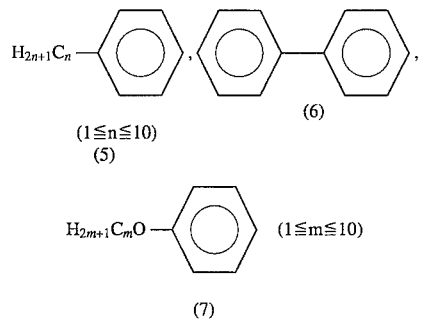

($1 \leq n \leq 10$)
(5) (6)

$H_{2m+1}C_mO$—◯  ($1 \leq m \leq 10$)

(7)

Furthermore, the positions where an azo group and oxygen bond to $R_1$ and $R_2$ which are aromatic compounds are not particularly limited. In order to obtain a stable azo metal complex, it is preferable that an azo group and oxygen bond to $R_1$ and $R_2$ which are aromatic compounds in an ortho position.

Additionally, $R_3$ and $R_4$ in the foregoing structural formula 1 may be aromatic compounds or heterocyclic compounds as described above. Examples are compounds expressed by the following structural formulas 8 to 16.

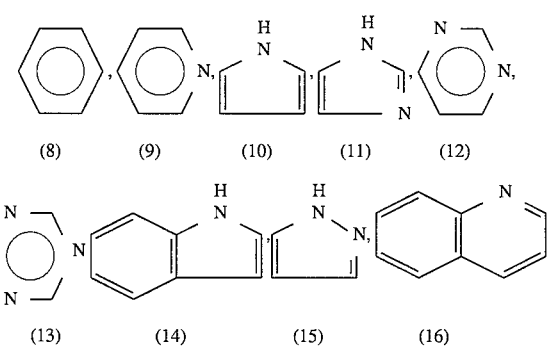

(8) (9) (10) (11) (12)

(13) (14) (15) (16)

Each of the compounds expressed by the foregoing structural formulas 8 to 16 may have a substituting group. A substituting group having electron donative properties is generally favorable as such a substituting group. In addition, it is preferable that the substituting group does not cause steric hindrance if an azo metal complex is produced by coordinating the compound to the above described metal M or if the odorous material is brought into contact with the metal M in the azo metal complex.

Furthermore, if the above described $R_3$ and $R_4$ are heterocyclic compounds and particularly, heterocyclic compounds containing nitrogen, and the above described metal M is a transition metal element such as Fe, Co, Mn or Ni allowing four or more coordinate bonds, it is preferable that $R_3$ and $R_4$ are coordinated to the metal M, as expressed by the following structural formula 17.

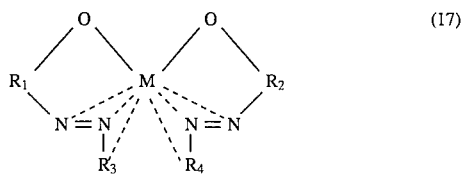

Furthermore, in the present invention, it is preferable that a divalent metal salt is used as a metal salt with the above described metal M in producing the azo metal complex expressed by the foregoing structural formula 1. This is for preventing a portion which bonds to the metal M from causing steric hindrance in mixing a solution in which the metal salt is dissolved with a solution in which azo compounds are dissolved to produce the azo metal complex expressed by the foregoing structural formula 1. Lead acetate, oxalate, lactate or the like can be used as the metal salt with the metal M.

Concrete examples in the present invention will be described in detail, and a comparative example is given to reveal that deodorants in the examples in the present invention are superior.

EXAMPLE 1

In this example, in synthesizing an azo metal complex used for a deodorant, 4-(2-Pyridylazo)resorcinol (hereinafter abbreviated as PAR) expressed by the following structural formula 18 was used as azo compounds to be ligands, while copper was used as a metal M.

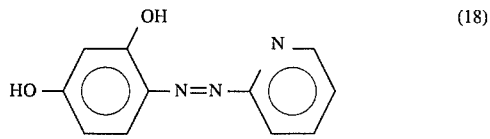
(18)

2.6 g (0.012 mole) of PAR was added to 150 ml of a methanol solution and was agitated while being heated at temperatures of 60° to 65° C. to be dissolved, while 1.2 g (0.006 mole) of copper acetate was added to 50 ml of a methanol solution and was agitated while being heated at temperatures of 60° to 65° C. to be dissolved.

The methanol solution in which PAR is dissolved and the methanol solution in which copper acetate is dissolved were then mixed with each other, and a mixed solution obtained was agitated for four hours under reflux of methanol. Consequently, a deposit having a red-black mixture was obtained, and this deposit was filtered and recovered.

As a result, 2.7 g (0.0055 mole) of a Cu-PAR complex having a composition ratio of 1:2 in which two PARs are coordinated to Cu as expressed by the following structural formula 19 was obtained, and the yield thereof was 92%.

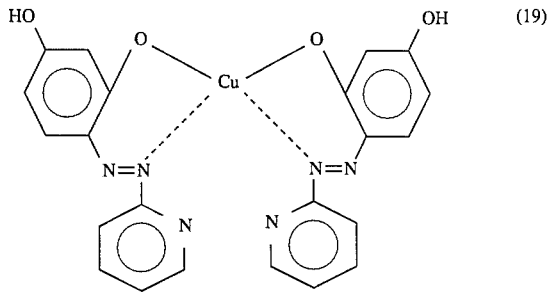
(19)

In this example, the Cu-PAR complex obtained in the above described manner was used for a deodorant.

EXAMPLE 2

In this example, in synthesizing an azo metal complex used for a deodorant, 1-(2-Pyridylazo)-2-naphthol (hereinafter abbreviated as PAN) expressed by the following structural formula 20 was used as azo compounds to be ligands, while cobalt was used as a metal M.

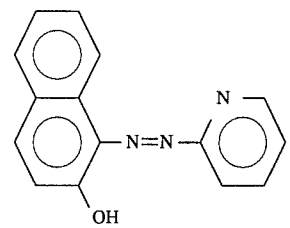
(20)

3.0 g (0.012 mole) of PAN was added to 150 ml of a methanol solution and was agitated while being heated at temperatures of 60° to 65° C. to be dissolved, while 1.5 g (0.006 mole) of cobalt acetate was added to 50 ml of a methanol solution and was agitated while being heated at temperatures of 60° to 65° C. to be dissolved.

The methanol solution in which PAN is dissolved and the methanol solution in which cobalt acetate is dissolved were then mixed with each other, and a mixed solution obtained was agitated for four hours under reflux of methanol. Consequently, a black deposit was obtained, and this deposit was filtered and recovered.

As a result, 3.1 g (0.0056 mole) of a Co-PAN complex having a composition ratio of 1:2 in which two PANs are coordinated to Co as expressed by the following structural formula 21 was obtained, and the yield thereof was 93%.

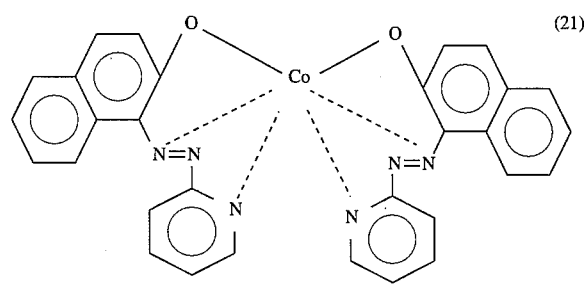
(21)

In this example, the Co-PAN complex obtained in the above described manner was used for a deodorant.

EXAMPLE 3

In this example, in synthesizing an azo metal complex used for a deodorant, the same PAN as that in the above described example 2 was used as azo compounds to be ligands, while iron was used as a metal M.

5.0 g (0.02 mole) of PAN was added to 250 ml of a methanol solution and was agitated while being heated at a temperature of 60° to be dissolved, while 1.7 g (0.006 mole) of iron acetate (II) was added to 100 ml of a methanol solution and was agitated while being heated at a temperature of 60° C. to be dissolved.

The methanol solution in which PAN is dissolved and the methanol solution in which iron acetate (II) is dissolved were then mixed with each other, and a mixed solution obtained was agitated for four hours under reflux of methanol. Consequently, a deposit having a black-green mixture was obtained, and this deposit was filtered and recovered.

As a result, 5.1 g (0.0092 mole) of a Fe-PAN complex having a composition ratio of 1:2 in which two PANs are coordinated to Fe as expressed by the following structural formula 22 was obtained and the yield thereof was 92%.

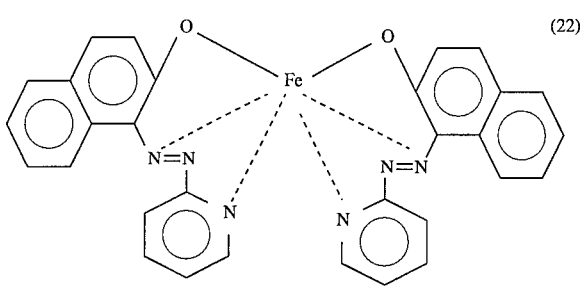

In this example, the Fe-PAN complex obtained in the above described manner was used for a deodorant.

In examining the deodorizing effect of the deodorant in each of the above described examples, N,N'-Bis (Salicylidene)ethylenediamine cobalt (II) expressed by the following structural formula 23 conventionally used was used for a deodorant in a comparative example for the purpose of comparison with the deodorants in the respective examples.

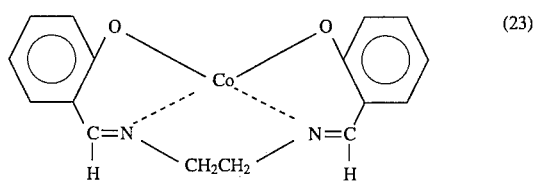

In examining the deodorizing effects of the deodorants in the above described examples 1 to 3 and the deodorant in the comparative example, the deodorizing rate for deodorizing hydrogen sulfide $H_2S$ which is a typical odorous material was measured by a method using a gas detector tube.

In measuring the deodorizing rates of the deodorants in the above described examples 1 to 3 and the comparative example, 1.2 g of the deodorants were respectively sealed in 8-litter sealed vessels, and each of the sealed vessels was filled with gas having a hydrogen sulfide concentration of 90 ppm, to measure the hydrogen sulfide concentration after five minutes, fifteen minutes, thirty minutes and sixty minutes. The results of the measurements are shown in FIG. 1.

In FIG. 1, the result obtained when the deodorant in the example 1 is used is indicated by ●, the result obtained when the deodorant in the example 2 is used is indicated by ○, the result obtained when the deodorant in the example 3 is used is indicated by ▲, and the result obtained when the deodorant in the comparative example is used is indicated by △.

As apparent from the results, the deodorizing rate for deodorizing hydrogen sulfide in the deodorant in each of the examples using the azo metal complexes expressed by the foregoing structural formulas 19, 21 and 22 is significantly improved, as compared with the deodorant in the comparative example using the metal complex expressed by the foregoing structural formula 23.

Although in the above described examples, Cu, Co or Fe is used as the metal in the azo metal complex, the metal used in the azo metal complex is not particularly limited to the same. For example, a transition metal element such as Mn or Ni can be also used. Also in this case, it is considered that approximately the same result as the above described result is obtained.

Furthermore, although in the above described examples, PAR or PAN is used as the azo compound which is coordinated to the metal M, the azo compound is not limited to the same. It is considered that the same results are obtained also in a case where the compounds expressed by the foregoing structural formulas 2 to 7 are used as $R_1$ and $R_2$ in the foregoing structural formula 1 and the compounds expressed by the foregoing structural formulas 8 to 16 are used as $R_3$ and $R_4$.

As described in the foregoing, in the deodorant according to the present invention, the azo metal complex expressed by the foregoing structural formula 1 is well exerted as a catalyst on the odorous material which causes a malodor or the like. Consequently, the odorous material is oxidized, to be removed simply and efficiently.

As a result, if the deodorant according to the present invention is used, there are no possibilities that the odorous material itself remains and the odorous material is discharged outward to cause secondary contamination as in the conventional example. Consequently, the odorous material which causes a malodor or the like can be removed safely and quickly. In addition, the odorous material can be removed stably for a long time, and the running cost may be low. In addition, even if the deodorant is not used in the state of an aqueous solution, the deodorizing effect which is superior to that of the conventional deodorant using metal phtalocyanine or a metal complex obtained by coordinating a Schiff base to a metal is obtained, thereby allowing superior deodorizing in various places.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method for deodorizing an odorous material which comprises oxidizing the odorous material to an odorless material in the presence of a catalyst of the formula

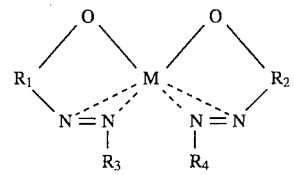

wherein M represents a transition metal element, $R_1$ and $R_2$ each represent a divalent aromatic radical, and $R_3$ and $R_4$ each represent a monovalent aromatic or heterocyclic radical.

2. A method according to claim 1, wherein the catalyst changes an odorous material to an odorless material in air.

3. A method according to claim 1, wherein M is Mn, Fe, Co, Ni or Cu.

4. A method according to claim 1, wherein $R_1$ and $R_2$ are divalent aromatic radicals derived from a compound of the formula

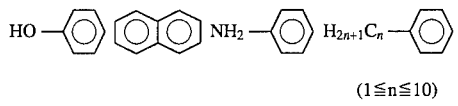
$(1 \leq n \leq 10)$

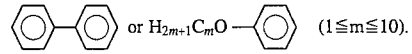  $(1 \leq m \leq 10)$.

5. A method according to claim 1, wherein $R_3$ and $R_4$ are monovalent aromatic or heterocyclic radicals derived from a compound of the formula

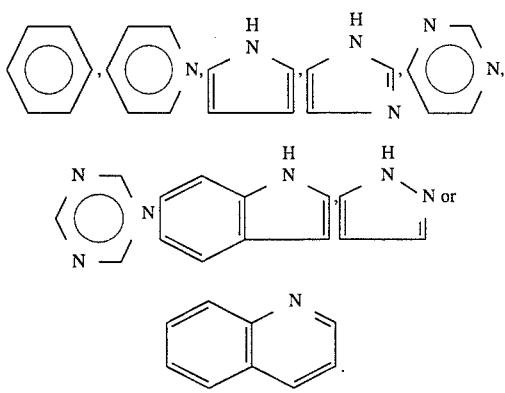

6. A method for deodorizing an odorous material which comprises oxidizing the odorous material to an odorless material in the presence of a catalyst of the formula

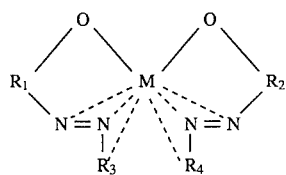

wherein M represents a transition metal element, $R_1$ and $R_2$ each represent a divalent aromatic radical, and $R_3$ and $R_4$ each represent a monovalent aromatic or heterocyclic radical.

7. A method according to claim 6, wherein the catalyst changes an odorous material to an odorless material in air.

8. A method according to claim 6, wherein M is Mn, Fe, Co, Ni or Cu.

9. A method according to claim 6, wherein $R_3$ and $R_4$ are monovalent radicals derived from a nitrogen-containing heterocyclic compounds.

10. A method according to claim 6, wherein $R_1$ and $R_2$ are divalent aromatic radicals derived from a compound of the formula

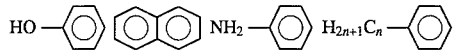

$(1 \leq n \leq 10)$

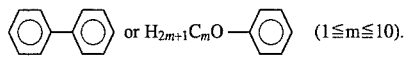

$(1 \leq m \leq 10)$.

11. A method according to claim 6, wherein $R_3$ and $R_4$ are monovalent aromatic or heterocyclic radicals derived from a compound of the formula

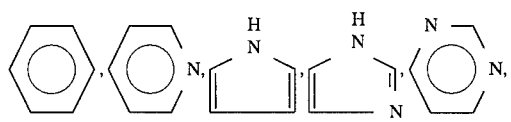

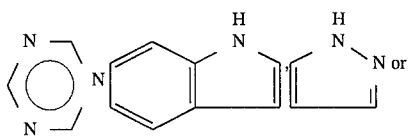

* * * * *